United States Patent [19]

O'Connor

[11] Patent Number: 4,902,438
[45] Date of Patent: Feb. 20, 1990

[54] LUBRICATING OIL COMPOSITIONS CONTAINING ANTI-WEAR/EXTREME PRESSURE ADDITIVES

[75] Inventor: Sean P. O'Connor, North Humberside, United Kingdom

[73] Assignee: Bp Chemicals Limited, London, United Kingdom

[21] Appl. No.: 190,595

[22] Filed: May 5, 1988

[30] Foreign Application Priority Data

May 12, 1987 [GB] United Kingdom ............... 8711191

[51] Int. Cl.$^4$ ............... C10M 135/24; C10M 135/26
[52] U.S. Cl. ............... 252/48.2; 252/48.6; 568/22; 568/26
[58] Field of Search ............... 252/48.2, 48.6; 568/22, 568/26

[56] References Cited

U.S. PATENT DOCUMENTS

| | | | |
|---|---|---|---|
| 2,520,748 | 8/1950 | Vaughan et al. | 252/48.6 |
| 2,562,144 | 7/1951 | Harman et al. | 252/48.6 |
| 3,041,283 | 6/1962 | Calhoun | 252/47 |
| 3,637,500 | 1/1972 | Forbes et al. | 252/48.6 |
| 4,036,709 | 7/1977 | Harbulak | 204/49 |
| 4,157,971 | 6/1979 | Yaffe et al. | 252/48.6 |
| 4,250,046 | 2/1981 | Przybylinski | 252/48.2 |
| 4,559,153 | 12/1985 | Baldwin et al. | 252/48.6 |

FOREIGN PATENT DOCUMENTS 2114653 10/1972 Fed. Rep. of Germany ........ 568/22

OTHER PUBLICATIONS

Journal of American Chemical Society, vol. 83, pp. 4644–4647, (1961) Hiskey et al.

*Primary Examiner*—William R. Dixon, Jr.
*Assistant Examiner*—Jerry D. Johnson
*Attorney, Agent, or Firm*—Brooks Haidt Haffner & Delahunty

[57] ABSTRACT

Compounds suitable for use as EP/AW additives in lubricating oil compositions which compounds have the formula:

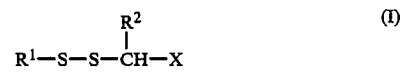

wherein
X is independently either a carboxylic acid group, a carboxylic acid ester group, a hydroxyl group or the group YZ wherein Z=X and Y is either an alkylene, aralkylene or cycloalkene group,
$R^1$ is an aliphatic hydrocarbyl group, and
$R^2$ is either hydrogen, a hydrocarbyl group or the group YZ.

11 Claims, No Drawings

LUBRICATING OIL COMPOSITIONS CONTAINING ANTI-WEAR/EXTREME PRESSURE ADDITIVES

The present invention relates to novel compounds useful as anti-wear/anti-corrosion additives in lubricating oil compositions, to a method for their preparation and to lubricating oil compositions containing the aforesaid additives.

The severe demands placed upon lubricating oils by modern internal combustion engines necessitate incorporation into the lubricating oil of additives of various types, for example viscosity index improvers, dispersants, detergents, anti-oxidants, anti-wear (A.W.) agents, extreme pressure (E.P.) agents, and the like. Generally, each additive agent is employed to impart a particular characteristic to the base oil so as to afford a finished lubricating oil composition which is oxidation resistant, stable and non-corrosive to bearing metals, and which effectively reduces varnish and sludge forming tendencies and minimises frictional and corrosive wear.

The use of zinc dialkyl dithiophosphates (ZDTPs) as additives in lubricating oils for the purpose of improving the wear and corrosion characteristics of the oil has long been known from, for example GB Pat. Nos. 957,017: 1,358,478 and 1,565,961.

Despite the fact that ZDTPs have been very effective and very successful in a number of engine lubricating oils, it is presently considered desirable to reduce the phosphorus content of the finished lubricating oil by the provision of alternative and/or supplementary additives for the purpose of reducing environmental pollution.

One class of compound proposed for this purpose are the hydrocarbon polysulphide derivatives of 2,5-dimercapto-1,3,4-thiadiazole having the general formula:

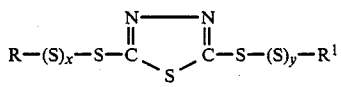

wherein R and $R^1$ are the same or different hydrocarbon radicals, x and y are numbers 0 to about 8, the sum of x and y is at least one, and preferably 2 to about 16. Such compounds are described in U.S. Pat. Nos. 2,719,125; 2,719,126 and 3,663,561. One of these compounds of formula:

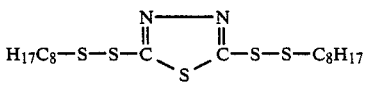

has achieved some commercial importance.

Another class of compounds useful as extreme pressure additives to lubricating oils is described in GB-A-2000130. These are (thio)acetal compounds of the formula:

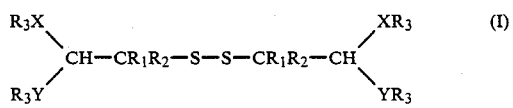

wherein $R_1$ and $R_2$ are 1-12 C alkyl or together form 4-7C alkylene; x and y are 0 or 5; $R_3$ is 1-18 C alkyl, 6-18C aryl, 7-9C aralkyl or wherein $R_1$ and $R_2$ are identical or different $C_1$-$C_{12}$ alkyl or together are $C_4$-$C_7$ alkylene, X and Y are identical or different and are each O or S and $R_3$ is a $C_1$-$C_{18}$ aryl, $C_7$-$C_9$ aralkyl, carboxy-($C_1$-$C_2$)-alkyl, ($C_1$-$C_{18}$-alkoxy)-carbonlyl-($C_1$-$C_2$-alkyl), N-$C_1$-$C_{18}$-alkylated carbamoyl-($C_1$-$C_2$)-alkyl or an ammonium salt of an amine with carboxymethyl or 2-carboxyethyl, or two $R_3$ radicals of an acetal/thioacetal group together are $C_2$-$C_4$ alkylene.

From SU-A-1216182 is known alkyl-dithia-alkane-diols, useful as anticorrosion additives to lubricating oils, having the formula:

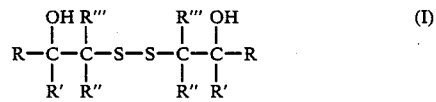

wherein R is Me or 2,2-dimethylpropyl; $R^1$ is Me, and $R^{11}$ and $R^{111}$ are H; or R is t-Bu, $R^1$ is H, and $R^{11}$ and $R^{111}$ are Me; or R is pentyl, $R^1$ and $R^{11}$ are H, and $R^{111}$ is Me; or R is hexyl, dodecyl or eicosyl and $R^1$, $R^{11}$, $R^{111}$ are H.

Finally, from EP-A-191983 is known dithio-alkano-amido-phenol compounds, useful for inhibiting oxidative and thermal degradation of organic polymers and oils, having the formula:

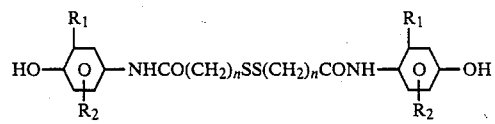

wherein
n=1-10,
$R_1$ = 1-10 C alkyl or 5-12C cycloalkyl,
$R_2$ = H, 1-8C alkyl or 5-12C cycloalkyl.

We have now found a class of novel compounds useful as anti-wear/extreme pressure additives in lubricating oil compositions.

Accordingly, the present invention provides compounds suitable for use as EP/AW additives in lubricating oils which compounds have the formula:

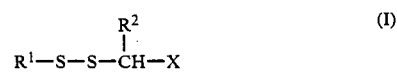

wherein
X is independently either a carboxylic acid group, a carboxylic acid ester group, a hydroxyl group or the group YZ wherein Z=X and Y is either an alkylene, aralkylene or cycloalkene group,
$R^1$ is an aliphatic hydrocarbyl group, and
$R^2$ is either hydrogen, a hydrocarbyl group or the group YZ.

In the formula (I), $R^1$ is suitably an alkyl group, preferably an alkyl group having at least 6 carbon atoms, Y is preferably an alkylene group and $R^2$ is either hydrogen, a hydrocarbyl group which is suitably an alkyl group, for example methyl, ethyl or propyl or the group YZ wherein Z is preferably a carboxylic acid group.

Examples of suitable compounds having the formula (I) are alkyldithioalkanoic acids (X=—COOH) wherein $R^1$ is either n-octyl or n-dodecyl and $R^2$ is either hydrogen or methyl, alkyldithioalkanoic acid esters (X=—COOC$_2$H$_5$) wherein $R^1$ is n-octyl and $R^2$ is hydrogen, 2-alkyldithioethanols (X=—CH$_2$OH) wherein R$^1$=n-octyl and R$^2$=H and alkyldithiosuccinic acids (X=—COOH) wherein R$^1$=n-dodecyl and R$^2$=—CH$_2$COOH.

The present invention also provides a process for the production of compounds having the formula (I) which process comprises the steps of:

(A) reacting a thiol of the formula R$^1$SH (II) wherein R$^1$ has the same significance as in the formula (I) with thiourea and hydrogen peroxide in aqueous alcoholic media in the presence of a salt-forming acid to produce a salt of the formula:

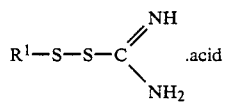   (III)

(B) reacting the salt of formula (III) with a compound of the formula:

   (IV)

wherein R$^2$ and X have the same significance as in the formula (I) in aqueous alcoholic media under basic conditions to produce the compound of formula (I), and (C) recovering the compound of formula (I) produced in step (B).

Further details of step (A) of the process may be found in Chem. Pharm. Bull., 1970, 18(2), 235–242, the disclosure of which is incorporated by reference herein.

In step (A) of the process there is employed an alcohol. Suitable alcohols include aliphatic and aromatic alcohols, alcohol ethers, polyols, and the like. Preferably the alcohol is a C$_1$ to C$_4$ alkanol, for example methanol or ethanol. The acid may suitably be any acid which forms an acid salt, and may be either a mineral acid or an organic acid, preferably a mineral acid. Suitable acids are those of the formula HX wherein X is halide, for example chloride. Step (A) may suitably be carried out at sub-ambient, ambient or elevated temperature, preferably at a temperature in the range 0° to 25° C.

In step (B) of the process there is employed an alcohol, which may be the same or different to the alcohol employed in step (A). The reaction is carried out under basic conditions, which may be accomplished by addition of an organic or inorganic base, preferably an inorganic base, for example sodium bicarbonate. The reaction may suitably be carried out at sub-ambient, ambient or elevated temperature, preferably in the range from 0° C. to the reflux temperature of the alcohol.

In step (C) the compound of formula (I) is recovered. This may be accomplished in conventional manner.

The present invention also provides a finished lubricating oil composition comprising a lubricating oil base stock and an EP/AW improving amount of a compound of the formula (I).

The lubricating oil base stock may be any oil of lubricating viscosity, which may be a mineral oil or a synthetic lubricating oil. Suitable mineral oils include both solvent extracted or solvent refined oils obtained in accordance with conventional methods of treating lubricating oils. The base oil may be derived from paraffinic, naphthenic, asphaltic or mixed base crudes. Alternatively, the base oil may be a synthetic oil, or a mixture thereof with mineral oil.

The lubricating oil composition may suitably contain from 0.01 to 10, preferably from 0.1 to 1% w/w of the compound of formula (I), the remainder of the composition being comprised of the lubricating oil base stock.

In addition, the lubricating oil composition may contain conventional additives, for example dispersants, detergents, VI improvers, anti-oxidants, pour-point depressants, or the like.

Lubricating oil additives are generally manufactured and marketed in the form of a concentrate for subsequent blending into finished lubricating oils.

In another embodiment of the invention there is provided a lubricating oil additive concentrate for use in the production of finished lubricating oils which comprises a lubricating oil base stock and sufficient of a compound of formula (I) to give a concentration of from 0.01 to 10, preferably from 0.1 to 1, %w/w in the finished lubricating oil composition.

Suitably the concentration of the compound of formula (I) in the concentrate composition may be from 2 to 20, typically about 10, times its concentration in the finished lubricating oil composition.

The lubricating oil base stock may be any of the aforedescribed lubricating oils, but is preferably a solvent neutral oil. As an alternative to incorporating conventional additives directly in the finished lubricating oil composition some or all of them may be incorporated with the compound of formula (I) in the concentrate composition.

The invention will now be further illustrated by reference to the following examples.

PREPARATION OF COMPOUNDS OF THE FORMULA (I)

EXAMPLE 1

Step (A)—Production of S-n-octylthioisothiourea hydrochloride, i.e. R$^1$=n-octyl Hydrogen peroxide (30% aqueous, 28.0 g) was added dropwise over 45 minutes to a stirred mixture of n-octanethiol (32.27 g, 0.221 mole), thiourea (20.1 g, 0.264 mole), concentrated hydrochloric acid (35 ml), water (35 ml) and ethanol (500 ml) maintained at 0°–10° C. After the addition was complete the reaction mixture was stirred at room temperature for 2 hours during which time a thick white precipitate formed. The mixture was filtered and the filtrate evaporated giving a solid residue. This was dissolved in ethanol (150 ml), diluted with diethyl ether (800 ml) and allowed to stand overnight at 0° C. Filtration gave white crystals of the product (46.3 g; 82%), melting point=77°–82° C.

Steps (B) and (C)—(R$^2$=H; X=COOC$_2$H$_5$)

The product of step (A) was reacted with HS—CH$_2$—COOC$_2$H$_5$ in a similar manner to that described in Example 2.

EXAMPLE 2

Step (A)—Production of S-n-dodecylthioisothiourea hydrochloride, i.e. R$^1$=n-dodecyl n-Dodecylthiol was reacted with thiourea and concentrated hydrochloric acid in a manner similar to that described in Example 1, step (A).

Steps (B) and (C)—(R$^2$=CH$_3$; X=COOH)

A solution of sodium bicarbonate (5.26 g; 0.061 mole) in water (100 ml) was added dropwise over 1 hour to a stirred solution of thiolactic acid (3.24 g; 0.0306 mole)

and S-n-dodecylthioisothiourea hydrochloride prepared in step (A) (9.55 g; 0.0306 mole) in methanol (100 ml) at room temperature. Foaming was observed and a white precipitate formed. The mixture was stirred at room temperature for a further 4 hours, then acidified (50% hydrochloric acid) and filtered. The solid was washed with water and dried giving the product in the form of a white solid (7.75 g, 83%), melting point=48°-51° C.

EXAMPLES 3–7

The following compounds of formula (I) were prepared by a similar procedure to that described in Examples 1 and 2:
Example 3—$R^1$=n-dodecyl; $R^2$=H; X=COOH.
Example 4—$R^1$=n-octyl; $R^2$=$CH_3$; X=COOH.
Example 5—$R^1$=n-octyl; $R^2$=H; X=COOH.
Example 6—$R^1$=n-octyl; $R^2$=H; X=$CH_2OH$.
Example 7—$R^1$=n-dodecyl; $R^2$=$CH_2COOH$; $R^3$=COOH.

The identities of the substituents for the products of Examples 1-7 are given in the following Table 1.

TABLE 1

| Example | $R^1$ | $R^2$ | X |
|---|---|---|---|
| 1 | n-octyl | H | $COOC_2H_5$ |
| 2 | n-dodecyl | $CH_3$ | COOH |
| 3 | n-dodecyl | H | COOH |
| 4 | n-octyl | $CH_3$ | COOH |
| 5 | n-octyl | H | COOH |
| 6 | n-octyl | H | $CH_2OH$ |
| 7 | n-dodecyl | $CH_2COOH$ | COOH |

PRODUCT TESTING

EXAMPLES 8–12

Blends of the products of Examples 1-4 and 6 were made up in SN 150 base oil and the anti-wear properties of the blends were tested using the Shell four-ball test. This test involved pressing a rotating steel ball against a triangle of three stationary balls lubricated with the blend under test. The Initital Seizure Load (ISL), the scar diameter (40 Kg/one hour) and the Weld Load (WL) were determined.

The copper strip ratings of the blends were also determined at 150° C. after 3 hours in conventional manner.

COMPARISON TEST A

The procedure of Examples 8-12 was used except that no additive was employed.

COMPARISON TEST B

The procedure of Examples 8-12 was used except that instead of a compound of formula (I) there was used a commercially available thiadiazole ashless EP/AW agent.

COMPARISON TEST C

The procedure of Examples 8-12 was used except that instead of a compound of formula (I) there was used a commercially available zinc dialkyl dithiophosphate (ZDTP1).

COMPARISON TEST D

The procedure of Examples 8-12 was used except that instead of the compound of formula (I) there was used a different commercially available zinc dialkyl dithiophosphate (ZDTP2).

Comparison Tests A-D are not examples according to the present invention because no compound of the formula (I) was employed. They are included only for the purpose of comparison.

The results of the four-ball tests and the copper strip rating determinations are given in Table 2.

TABLE 2

| | | | Four-ball test | | | Copper strip rating |
|---|---|---|---|---|---|---|
| | | Concn | ISL | | WL | |
| Example | Product | (%) | kg | scar (mm) | kg | 150° C./3 hours |
| Comp Test A | SN 150 | — | 40 | 1.30 | 120 cat* | 3A |
| 8 | 1 | 1 | 50 | 0.69 | 220 | 3A (0.1%) |
| 9 | 2 | 0.1 | 80 | 2.31 | 150 | 2A |
| 10 | 3 | 0.1 | 100 | 2.22 | 160 cat* | 3B |
| 11 | 4 | 0.1 | 80 | 0.397 | 170 | 2C |
| 12 | 6 | 0.1 | 60 | 1.85 | 160 | 1B |
| Comp Test B | ** | 0.1 | 70 | 1.70 | 160 | 3A |
| Comp Test C | ZDTP | 0.1 | 40 | 1.50 | 130 cat* | 3A (1%) |
| Comp Test D | ZDTP | 0.1 | 55 | 1.90 | 150 cat* | 3A (1%) |

*cat - indicates catastrophic wear at this load.
**commercial thiadiazole.

With reference to Table 2, the copper strip ratings are as follows:
1A–1B—Slight tarnish
2A–2E—Moderate tarnish
3A–3B—Dark tarnish
4A–C—Corrosion.

The results shown in Table 2 demonstrate that the majority of the compounds of formula (I) tested are better in terms of EP/AW properties than the ZDTPs in the four-ball test and some, e.g. the product of Example 4, are comparable or better than the commercial thiadiazole ashless inhibitor. All the compounds tested are comparable or better than the ZDTPs and commercial thiadiazole in the copper strip test.

I claim:
1. Compounds suitable for use as EP/AW additives in lubricating oil compositions which compounds have the formula:

wherein
X is independently a carboxylic acid group, a hydroxyl group or the group YZ wherein Z is a carboxylic acid group or a hydroxyl group is an alkylene group, $R^1$ is an alkyl group having at least 6 carbon atoms, and $R_2$ is hydrogen, a methyl, ethyl or propyl group or the group YZ.

2. Compounds according to claim 1 wherein in the formula (I) $R^2$ is hydrogen, a methyl, ethyl or propyl group, or the group YZ wherein Z is a carboxylic acid group.

3. Compounds according to claim 1 wherein the formula (I) $R^1$ is either n-octyl or n-dodecyl, $R^2$ is either hydrogen or methyl and X is —COOH.

4. Compounds according to claim 1 wherein in the formula (I) $R^1$ is n-octyl, $R^2$ is hydrogen and X is —CH$_2$OH.

5. Compounds according to claim 1 wherein in the formula (I) $R^1$ is n-dodecyl, $R^2$ is —CH$_2$COOH and X is —COOH.

6. A process for the production of the compounds of formula (I) as claimed in claim 1 which process comprises the steps of:

(A) reacting a thiol of the formula $R^1SH$ (II) wherein $R^1$ has the same significance as in the formula (I) with thiourea and hydrogen peroxide in aqueous alcoholic media in the presence of a salt-forming acid to produce a salt of the formula:

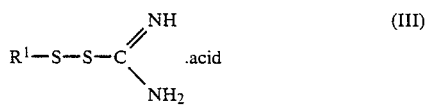

(B) reacting the salt of formula (III) with a compound of the formula:

wherein $R^2$ and X have the same significance as in the formula (I) in aqueous alcoholic media under basic conditions to produce the compound of formula (I), and (C) recovering the compound of formula (I) produced in step (B).

7. A finished lubricating oil composition comprising a lubricating oil base stock and an EP/AW improving amount of a compound of the formula (I) as claimed in claim 1.

8. A finished lubricating oil composition according to claim 7 containing from 0.1 to 1% w/w of the compound of formula (I).

9. A lubricating oil additive concentrate for use in the production of a finished lubricating oil composition with comprises a lubricating oil base stock and 0.02 to 200% w/w of a compound of formula (I) as claimed in claim 1.

10. A lubricating oil additive concentrate according to claim 9 containing 0.1 to 100% w/w of the compound of formula (I).

11. A finished lubrication oil composition according to claim 7 containing from 0.01 to 10% w/w of the compound of formula (I).

* * * * *

UNITED STATES PATENT AND TRADEMARK OFFICE
CERTIFICATE OF CORRECTION

PATENT NO. : 4,902,438

DATED : February 20, 1990

INVENTOR(S) : Sean P. O'Connor

It is certified that error appears in the above-identified patent and that said Letters Patent is hereby corrected as shown below:

Col. 5, line 2, should read "(9.55 g; 0.0306 mole)"

Claim 1, line 9, after "hydroxyl group" and before is"

insert --and Y--

Claim 11, line 1, change "lubrication" to --lubricating--

Signed and Sealed this

Ninth Day of April, 1991

Attest:

HARRY F. MANBECK, JR.

*Attesting Officer*

*Commissioner of Patents and Trademarks*